United States Patent [19]
Heck et al.

[11] Patent Number: 5,584,869
[45] Date of Patent: Dec. 17, 1996

[54] FAILURE DETECTION IN AUDITORY RESPONSE STIMULATORS

[75] Inventors: Patrice L. Heck, Yorba Linda, Calif.; Dianne Allum-Mecklenburg, Basel, Switzerland; Joseph H. Schulman, Santa Clarita, Calif.

[73] Assignee: Advanced Bionics Corporation, Sylmar, Calif.

[21] Appl. No.: 388,193

[22] Filed: Feb. 13, 1995

[51] Int. Cl.$^6$ ............................................. A01N 1/36
[52] U.S. Cl. ............................................................ 607/57
[58] Field of Search ........................ 607/32, 56, 57; 128/903

[56] References Cited

U.S. PATENT DOCUMENTS

| | | | |
|---|---|---|---|
| 3,902,478 | 9/1975 | Konopasek et al. | 128/903 |
| 3,953,848 | 4/1976 | Dillman et al. | 128/903 |
| 4,522,209 | 6/1985 | Patrick et al. | 607/57 |
| 4,675,656 | 6/1987 | Narcisse | 128/903 |
| 4,918,745 | 4/1990 | Hutchison | 455/41 |
| 5,024,224 | 6/1991 | Engebretson | 607/57 |
| 5,266,919 | 11/1996 | Cook | 340/384 E |

FOREIGN PATENT DOCUMENTS 0627194   3/1994   European Pat. Off. .
680249    7/1992   Switzerland .

*Primary Examiner*—William E. Kamm
*Attorney, Agent, or Firm*—Fitch, Even, Tabin & Flannery

[57] ABSTRACT

A system and method for detecting failures in an auditory stimulation device includes, in one embodiment, a microphone; a signal processor; a supercutaneous transmitter; a subcutaneous receiver; a subcutaneous transmitter; and a supercutaneous receiver. The signal processor generates a stimulation signal in response to the microphone detecting an audio signal, and the supercutaneous transmitter couples the stimulation signal through a skin surface of a patient. The subcutaneous receiver receives the stimulation signal, and the subcutaneous transmitter generates a feedback signal in response to receipt of the stimulation signal by the subcutaneous receiver. The supercutaneous receiver receives the feedback signal. In one variation of the embodiment, the signal processor generates an alarm signal when the feedback signal is not received. In another variation of the embodiment, the signal processor analyzes differences between the stimulation signal and the feedback signal, and generates a difference signal indicative of the differences between the stimulation signal and the feedback signal. The signal processor then generates the alarm signal in the event the difference signal indicates the differences exceed a prescribed threshold.

15 Claims, 3 Drawing Sheets

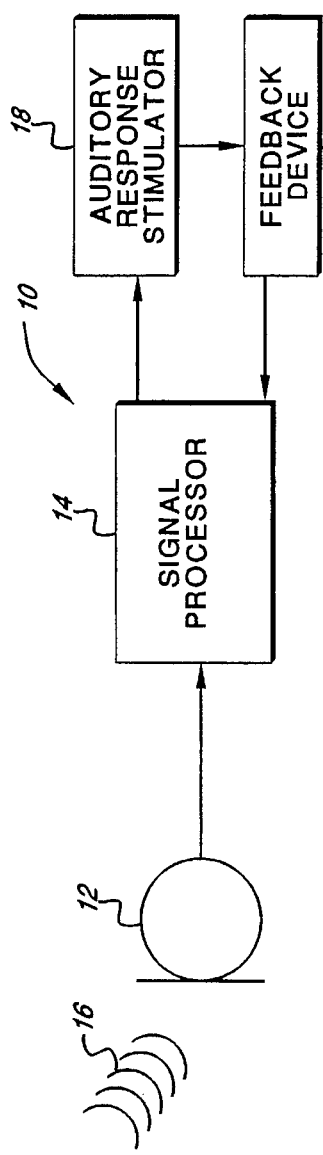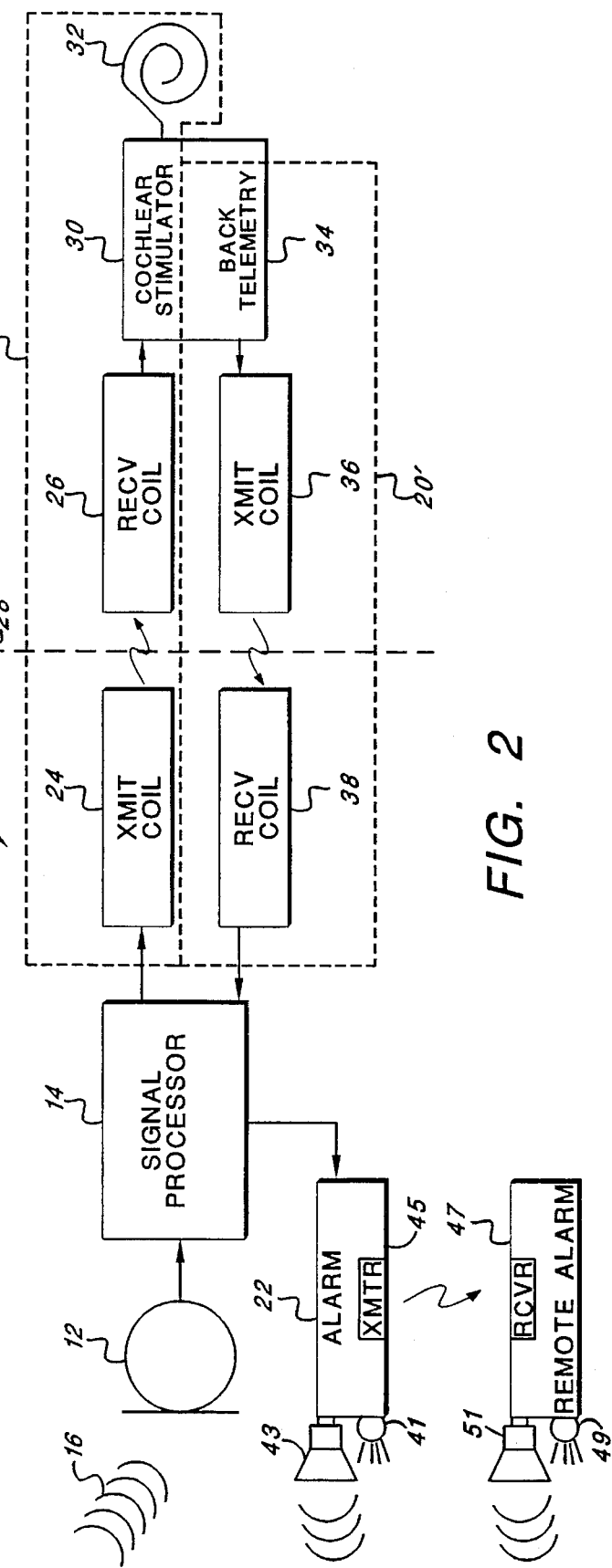

1

FAILURE DETECTION IN AUDITORY RESPONSE STIMULATORS

BACKGROUND OF THE INVENTION

The present invention relates to failure detection in auditory response stimulators, and more particularly to closed-loop feedback systems and methods for failure detection and reporting in auditory response stimulators. Even more particularly, the present invention relates to closed-loop feedback subsystems for detecting failure in hearing aides and cochlear implants, and for reporting such failure.

Over the past several years medical science has made great strides to improve the hearing assistance available to both partially deaf and profoundly deaf individuals. For example, individuals who were once completely unable to hear now may be able to hear with the aid of a specialized neural stimulation device referred to herein as a cochlear stimulator. Cochlear stimulators typically include a microphone and a signal processor. The microphone detects pressure waves or audio signals and the signal processor processes the detected pressure waves and generates a stimulation signal in response thereto. The stimulation signal is passed through the skin of the individual using a transcutaneous electromagnetically coupled transmitter/receiver coil pair. The stimulation signal is then further processed within the body and passed to an intracochlear electrode, which passes an electrical current to the auditory nerve within the cochlea of the individual. As a result, the individual experiences a hearing sensation or auditory sensation.

Similarly, individuals who are partially deaf, or hard of hearing, are now able to hear through the use of amplifier-type hearing aids. In such devices, pressure waves or audio signals are detected by a microphone that is typically housed in a package that is fitted into the outer ear canal, or behind the pinna (or auricle). The microphone detects pressure waves or acoustic signals and an amplifier within the housing amplifies the pressure waves in the form of a stimulation signal. The stimulation signal is passed to a speaker that is positioned within the outer ear canal and stimulation waves, i.e., amplified sounds, are generated in response thereto. The stimulation waves are directed down the outer ear canal and impact upon the tympanic membrane, tympanum, or eardrum.

Devices for stimulating hearing or auditory sensations are referred to herein generally as auditory response stimulation systems.

These devices and others have now made it possible for children and adults, who once required specialized teaching environments in order to receive educational instruction, to receive their education along with hearing students in a conventional classroom environment. Unfortunately, however, currently available devices for stimulating a hearing sensation in partially or profoundly deaf individuals are prone to occasional malfunction or failures, which result in a partial or complete loss of the individual's hearing. Such malfunction can be as a result of, e.g., component failure, decoupling of the transcutaneous electromagnetic coupling of the cochlear implant, or voltages or currents being supplied to intracochlear stimulation electrodes that are below a prescribed threshold. Such malfunction often goes undetected by the partially or profoundly deaf individual, because he or she does not hear when the apparatus is malfunctioning.

Thus, what is needed is a way to detect such malfunctions and to make these malfunctions known to the partially or profoundly deaf individual, or to, e.g., an instructor or lecturer who is leading the educational instruction or delivering a speech.

SUMMARY OF THE INVENTION

The present invention advantageously addresses the needs above as well as other needs by providing a closed-loop feedback subsystem for detecting failure in auditory response stimulation systems, such as hearing aides and cochlear implants, and for reporting such failure.

The invention may be characterized in one embodiment as a method for detecting failures in an auditory response stimulation system that includes an external wearable processor (WP) and an implanted cochlear stimulator (ICS). The method includes the steps of: detecting an audio signal, generating a stimulation signal in response to the detecting of the audio signal, telemetering the stimulation signal through a skin surface of a patient, the implantable cochlear stimulator using a supercutaneous transmitter, and detecting whether the stimulation signal is received into a subcutaneous receiver within the implantable cochlear stimulator. The method further includes generating a feedback signal within the implantable cochlear stimulator only when the stimulation signal is received into the subcutaneous receiver, and telemetering the feedback signal back through the skin surface of the patient using a subcutaneous transmitter to a supercutaneous receiver associated with the wearable processor.

In a first variation, the method also includes the step of detecting whether the feedback signal is received into the supercutaneous receiver, and generating an alarm signal in the event it is not.

In a second variation, the method further includes receiving the feedback signal into the supercutaneous receiver, analyzing differences between the transmitted stimulation signal and the received feedback signal, and generating a difference signal in response thereto. In the event the difference signal indicates that the differences between the stimulation signal and the feedback signal exceed a prescribed threshold, then an alarm signal is generated.

The invention may also be characterized, in a second embodiment, as a system for detecting failure in an auditory response stimulation system, where such system comprises a microphone; a signal processor; a supercutaneous transmitter; a subcutaneous receiver; a subcutaneous transmitter; and a supercutaneous receiver. In such system, the signal processor is coupled to the microphone, and includes means for generating a stimulation signal in response to the microphone detecting an audio signal. The supercutaneous transmitter is coupled to the signal processor, and includes means for coupling the stimulation signal through the skin to the subcutaneous receiver. Coupled to the subcutaneous receiver is the subcutaneous transmitter, which includes means for generating a feedback signal in response to receipt of the stimulation signal by the subcutaneous receiver. The supercutaneous receiver includes means for receiving the feedback signal, and is coupled to the signal processor.

In a variation of the second embodiment, the signal processor further includes means for generating an alarm signal in the event the feedback signal is not received into the supercutaneous receiver. In another variation, the signal processor includes means for analyzing differences between the stimulation signal and the feedback signal, and for generating a difference signal in response thereto. In the event the difference signal indicates that the differences between the stimulation signal and the feedback signal exceed a prescribed threshold, then the signal processor generates an alarm signal.

The invention can further be characterized, in a third embodiment, as a method for detecting failure in an auditory response stimulation system comprising: detecting an audio signal; generating a stimulation signal as a function of the detected audio signal; generating a feedback signal in the event an auditory response stimulator attempts to stimulate an auditory response in response to the stimulation signal; and generating an alarm signal in the event the audio signal is detected and feedback signal is not generated.

The invention can also further be characterized, in a fourth embodiment, as a system for detecting failure in an auditory response stimulation system comprising: a microphone; a signal processor coupled to the microphone; an auditory response stimulator; a feedback device; and means for generating an alarm signal.

The signal processor generates a stimulation signal in response to the microphone detecting an audio signal, and the auditory response stimulator is capable of stimulating an auditory response in response to the stimulation signal. The feedback device generates a feedback signal in the event the auditory response stimulator attempts to stimulate an auditory response in response to the stimulation signal, and the means for generating the alarm signal generates the alarm signal in the event the audio signal is detected and the feedback signal is not generated.

It is therefore a feature of the invention to provide for the detection of failures in an auditory response stimulation system.

It is a further feature of the invention to utilize a closed-loop feedback path in the detecting of such failure.

It is another feature of the invention to report such failures to the individual using the auditory response stimulation system and/or to another individual.

BRIEF DESCRIPTION OF THE DRAWINGS

The above and other aspects, features and advantages of the present invention will be more apparent from the following more particular description thereof, presented in conjunction with the following drawings wherein:

FIG. 1 is a block diagram of an auditory response stimulation system including features of the present invention;

FIG. 2 is a block diagram of a cochlear implant embodiment of the auditory response stimulation system of FIG. 1;

Corresponding reference characters indicate corresponding components throughout the several views of the drawings.

DETAILED DESCRIPTION OF THE INVENTION

Figure 3:
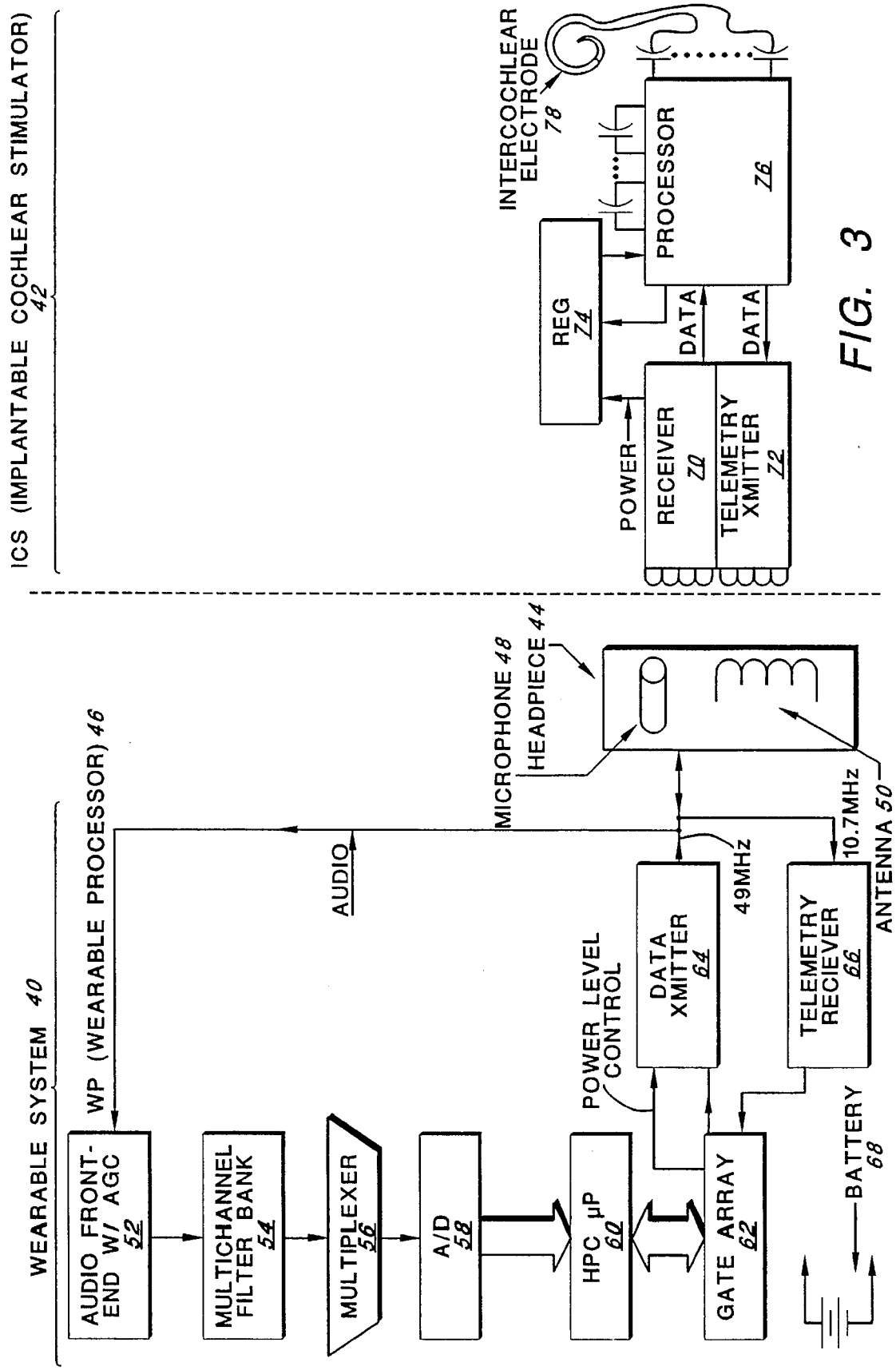
FIG. 3 is a more detailed block diagram of the cochlear implant embodiment of the auditory response stimulator of FIG. 2.

The following description of the presently contemplated best mode of practicing the invention is not to be taken in a limiting sense, but is made merely for the purpose of describing the general principles of the invention. The scope of the invention should be determined with reference to the claims.

Referring first to FIG. 1, a block diagram is shown of an auditory response stimulation system 10 made in accordance with the present invention. The system includes a microphone 12 that is shown coupled to a signal processor 14. The microphone 12 generates a microphone signal in response to a pressure wave 16, e.g., a sound wave or audio signal, as is known in the art. The signal processor 14 processes the microphone signal, as required by the particular application of the present invention. For example, the signal processor 14 may include a bank of band-pass filters that divides the microphone signal into a plurality of, e.g., eight, frequency bands or channels that may be used to stimulate a corresponding plurality of intracochlear electrodes used in a cochlear stimulator. In another example, the signal processor 14 may include an amplifier, such as would be the case if the present invention were utilized in a conventional amplifier-type hearing aid.

The signal processor 14 is detachably coupled to an auditory response stimulator 18, which may be, e.g., one or more intracochlear electrodes, or a speaker. The signal processor 14 generates an appropriate stimulation signal as a function of the microphone signal. This stimulation signal is passed to the auditory response stimulator 18, which attempts to stimulate an auditory response in the patient, i.e., to stimulate hearing in the patent. The term "attempts to" is used herein to indicate that stimulation is applied to the patient, e.g., electrical neural stimulation or amplified acoustic stimulation. Whether or not such stimulation is in fact successful in inducing a hearing sensation in the patient should be understood to be distinct from whether the auditory response stimulator 18 has attempted to stimulate or induce such a response.

After receiving the stimulation signal, the auditory response stimulator 18 couples the stimulation signal to a feedback device 20 (or feedback circuitry), also coupled to the signal processor 14. That is, the feedback device 20 generates a feedback signal as a function of whether it detects the presence of the stimulation signal. Such feedback signal is passed to the signal processor 14. The feedback signal thus indicates to the signal processor 14 whether the stimulation signal is present at the auditory response stimulator 18 as sensed by the feedback device 20. If the presence of the stimulation signal is not sensed by the feedback device 20 (as would be the case if, e.g., the auditory response stimulator 18 becomes decoupled from the signal processor 14), the feedback signal is not generated, and the signal processor 14 is thus made aware that a failure has occurred, e.g., that the auditory response stimulator 18 failed to pass the stimulation signal to the feedback device 20. The signal processor 14 then generates an alarm signal whenever the feedback signal is not received.

Alternatively or additionally, the feedback signal may be used to send information to the signal processor 14 regarding the operation of the auditory response stimulator 18. For example, the feedback signal may be used to send voltage and/or current measurements taken from intracochlear stimulation electrodes in the auditory stimulation device to the signal processor 14. In the event the voltages and/or currents are, e.g., too low, the feedback signal may include a low voltage or low current flag, as appropriate. The low voltage and/or low current flags, when received by the signal processor 14, may thus also trigger the generation of an alarm signal by the signal processor 14. Alternatively, the receipt of a low voltage and/or low current measurement at the signal processor 14 may directly trigger the generation of the alarm signal.

As thus described, the failure detection device of the present invention is able to detect a failure of the auditory response stimulator 18 to either pass the stimulation signal to the feedback device and/or to properly stimulate a hearing sensation in the patient.

In one variation of the invention, the stimulation signal carries information to the auditory response stimulator 18 indicative of the pressure waves 16 received by the microphone 12. As the stimulation signal passes from the signal processor 14 through the auditory response stimulator 18 via, e.g., a transcutaneous communications channel, noise and other distortions may be added to the stimulation signal, thereby distorting the information contained in the stimulation signal. Advantageously, the invention overcomes problems caused by these distortions, e.g., a distorted hearing sensation, by passing the information back to the signal processor 14 in the feedback signal. Once the distorted information is back in the signal processor 14, it is compared with the undistorted information that was passed by the signal processor 14 in the stimulation signal. By comparing the distorted information with the undistorted information, a determination is made as to how much distortion has been introduced, thereby allowing a signal to noise ratio (SNR) to be determined. Whenever the SNR falls below a prescribed threshold, or whenever other prescribed disparities are noted between the stimulation signal and feedback signal, the alarm signal is generated. The alarm signal in this variation, thus indicates that the stimulation signal received by the auditory response stimulator 18, may be so distorted as to doubt the reliability of the information contained therein.

Thus, the present invention provides for the detection and reporting of not only the failure of the auditory response stimulator 18 to receive and pass along the stimulation signal, but also the failure of the auditory response stimulator 18 to receive and pass along the stimulation signal having less than a prescribed threshold of difference from the stimulation signal before being passed through the auditory response stimulator 18 by the signal processor 14.

Referring next to FIG. 2, a block diagram is shown of a cochlear stimulator embodiment of the auditory response stimulation system 10 of FIG. 1. The microphone 12 is shown coupled to the signal processor 14, which is in turn coupled to the auditory response stimulator 18' and the feedback device 20'. An alarm device 22 is also coupled to the signal processor 14, such as a light 41 and/or a buzzer 43, e.g., a piezo electric buzzer. In the event the signal processor 14 detects the absence of the feedback signal from the feedback device 20' the signal processor 14 generates the alarm signal, which is used to trigger the alarm device 22, i.e., to turn on the light 41 or to sound the buzzer 43, or to otherwise signal an alarm condition.

In this embodiment, the auditory response stimulator 18' includes a transmit coil 24 coupled to the signal processor 14. The stimulation signal is passed to the transmit coil 24, which generates, e.g., a magnetic field in response thereto. A receive coil 26 is magnetically (i.e., inductively) coupled to the transmit coil 24 and regenerates the stimulation signal in response to the magnetic field. In practice, the transmit coil 24 is a supercutaneous coil, while the receive coil 26 is a subcutaneous coil, with a skin surface 28 (represented by a dashed line) of a patient being interposed therebetween. Typically, the supercutaneous transmit coil 24 is housed in a supercutaneous plastic case that is attached to the signal processor 14 with an insulated cable. In operation, the supercutaneous plastic case is positioned at a location on the skin surface, beneath which the subcutaneous receive coil 26 is located. The subcutaneous receive coil 26 is typically housed in a subcutaneous ceramic and/or metal case that also houses electronic circuits, such as an implanted processor. Preferably, the subcutaneous receive coil 26 is housed in a ceramic case so as to minimize the currents induced in the case by the magnetic field that emanates from the supercutaneous transmit coil 24. The receive coil 26 is coupled to a cochlear stimulator 30, which is in turn coupled to at least one intracochlear stimulation electrode 32.

Also coupled to the cochlear stimulator 30 is feedback circuitry 20' including a back-telemetry circuit 34, which generates the feedback signal in response to the stimulation signal from the subcutaneous receive coil 26. The back-telemetry circuit 34 passes the feedback signal to another transmit coil 36, or subcutaneous transmit coil 36, which magnetically (or inductively) couples the feedback signal across the skin surface 28 to another receive coil 38, or supercutaneous receive coil 38, in a manner similar to that in which the supercutaneous transmit coil 24 and the subcutaneous receive coil 26 mentioned above pass the stimulation signal through the skin surface 28. In practice, the supercutaneous transmit coil 24 and the supercutaneous receive coil 38 can be housed together in the supercutaneous plastic housing, such as are known in the art. Similarly, the subcutaneous receive coil 26 and the subcutaneous transmit coil 36 can be housed together in the subcutaneous ceramic and/or metal housing, as are also known in the art. See, e.g., U.S. Pat. No. 4,991,582.

In practice, a single supercutaneous coil may be used as the supercutaneous transmit and receive coils 24, 38 and a single subcutaneous coil may be used as the subcutaneous transmit and receive coils 36, 26. Amplitude modulation, e.g., and differing carrier frequencies, can be used to pass the stimulation signal and the feedback signal across the skin surface 28 between the single supercutaneous coil and the single subcutaneous coil. Separate coils are generally preferred for the subcutaneous transmit and receive coils 36, 26, while a single supercutaneous coil is preferred to carry out the functions of the supercutaneous transmit and receive coils 24, 38. In practice, the stimulation signal is passed from the single supercutaneous coil to the subcutaneous receive coil 26 using a first amplitude modulated carrier signal of a first frequency, and the feedback signal is passed from the subcutaneous transmit coil 36 to the single supercutaneous coil using a second amplitude modulated carrier signal of a second frequency. The information in the stimulation signal and in the feedback signal is amplitude modulated onto the respective carrier frequencies.

Even though the coils 24, 26, 38, 36 may be combined as described above, such coils are hereafter referred to as four separate coils for purposes of this document.

The supercutaneous receive coil 38 passes the feedback signal to the signal processor 14. In the event the feedback signal is not generated (as might occur, e.g., when the subcutaneous receive coil 26 does not receive the stimulation signal), the signal processor 14 generates the alarm signal. As described above, the alarm signal is passed to the alarm device 22, and is used to signal the failure of the auditory response stimulator 18'.

Alternatively or additionally, the feedback signal may be used to send information to the signal processor 14 regarding the operation of the cochlear stimulator. Specifically, the feedback signal may be used to send voltage and/or current measurements taken from the intracochlear stimulation electrode 32 to the signal processor. In the event the voltage or current measurements are too low, the feedback signal may include a low voltage or low current flag. The low voltage or low current flag may alternatively be generated by the signal processor 14 in response to the low voltage or low current measurement. In response to the low voltage or low current flags, the signal processor generates the alarm signal and passes it to the alarm device 22.

The alarm device 22 may in practice be a light 41 and/or a buzzer 43, and may include a radio frequency transmitter 45 and a radio frequency receiver 47. The transmitter 45 may be directly coupled to the signal processor 14 while the receiver 47 and a remote light 49 and/or buzzer 51 may be located remotely therefrom. Thus, the failure in the cochlear stimulator can be reported at a location remote from the location at which the cochlear stimulator is utilized. For example, the receiver 47 may be located at a podium whereat the instructor or speaker is located. As a result, the instructor or speaker can be notified at the podium when a student or listener (i.e., the patient) has a failure in their cochlear stimulator. In this way, failures in auditory response stimulation devices, such as the cochlear stimulator of FIG. 2, can be detected and signaled.

Note that the auditory response stimulation device 10 of FIG. 2 may also perform the distortion, e.g., noise detection functions described above, by passing the information contained in the stimulation signal back to the signal processor 14 in the feedback signal. Once the distorted information is back in the signal processor 14, it is compared with the undistorted information passed in the stimulation signal. By comparing the distorted information with the undistorted information, a determination is made as to what level of distortion is being introduced by, e.g., the transcutaneous communications channel, and a signal-to-noise ratio (SNR) can be determined. When the SNR falls below a prescribed threshold, the alarm signal is generated to indicate that the stimulation signal is so distorted as to doubt the reliability of the information contained therein. In response to the alarm signal, the alarm device 22 is energized, thereby alerting the patient or other individual to the unreliability of the information contained in the stimulation signal.

Thus, the cochlear stimulator made in accordance with the present invention provides for the detection and reporting of not only the failure of the auditory response stimulator 18 to receive and pass along the stimulation signal, but the failure of the auditory response stimulator 18 to receive and pass along the stimulation signal having less than a prescribed threshold of distortion or noise.

Referring next to FIG. 3, a block diagram is shown of a multi-channel cochlear stimulator. The multichannel cochlear stimulator is substantially the same as the embodiment shown in U.S. patent application Nos. 07/411,563, filed Sep. 27, 1989, and 07/752,069, filed Aug. 29, 1991, both now abandoned, of Schulman et al., for human tissue stimulators, incorporated herein by reference.

As illustrated in FIG. 3, the basic system comprises an externally wearable system 40 and an implantable cochlear stimulator (ICS) 42. The external system 40 comprises a headpiece 44 and an externally wearable processor (WP) 46. The headpiece 44 may be worn behind the ear of a hearing impaired person and comprises a conventional microphone 48 and an antenna 50 for transmitting and receiving electromagnetic energy preferably in the form of radio frequency signals. Such coupling can be restricted to magnetic field coupling only by use of an electrostatic shield placed around the coils comprising the antenna 50. In addition, signals coupled from the implantable cochlear stimulator 42 to the wearable processor 46 at one carrier frequency, and signals coupled from the wearable processor 46 to the implantable cochlear stimulator 42 at another carrier frequency, can be transferred via a single coaxial cable between the headpiece 44 and the wearable processor 46. This can be accomplished by having tuned inductor-capacitor filters for each frequency at each end of the coaxial cable.

The wearable processor 46, powered by a battery 68, is adapted to receive audio signals received by the microphone 48 and to transmit such signals to conventional audio front-end circuitry 52. Typically, the front-end circuitry 52 features automatic gain control (AGC). The audio signals processed by the audio front-end circuitry 52 are transmitted to a bank of filters 54. The filters 54 divide the audio signals into respective frequency bands thereby generating a plurality of parallel audio signals. The audio signals are processed by a multiplexer 56 and converted to a series of digital signals by an analog-to-digital converter 58. The digital signals are then applied to a microprocessor 60. The filter bank 54 may also be implemented as a group of digital filters, for example in a digital signal processor integrated circuit. In this case the signal flow would be from the audio front-end and AGC circuit 52, through an anti-aliasing filter, to an analog-to-digital converter 58, then into a digital filter bank 54 and the general processing of the microprocessor 60.

The output of the microprocessor 60 is coupled through a custom gate array 62. The gate array 62 converts data received from the microprocessor 60 into a serial bit stream going to a data transmitter 64. The gate array 62 also converts data received from a telemetry receiver 66 and the microprocessor 60 to control the power level of, and data generated by, the data transmitter 64. The gate array 62 thus facilitates the feedback functions described in conjunction with FIGS. 1, 2 and 4.

As illustrated in FIG. 3, the implantable cochlear stimulator 42 includes a receiver 70 for receiving data transmissions from the wearable system 40, and a telemetry transmitter 72 for transmitting implantable cochlear stimulator status-indicating signals from the implantable cochlear stimulator 42 to the wearable system 40. For example, power level indicating signals transmitted by the telemetry transmitter 72 are received by the telemetry receiver 66 and processed in the microprocessor 60 and gate array 62 to generate signals controlling the power level of the transmissions from the transmitter 64 to the implantable cochlear stimulator 42, thereby providing a closed-loop system for optimizing the power levels of the transmission from the wearable system 40 to the implantable cochlear stimulator 42, and hence conserving the battery 68 and optimizing the voltages generated within the system 40. The power level indicating signals may also serve as the feedback signal described herein.

In addition to the receiver 70 and transmitter 72, the implantable cochlear stimulator 12 includes a regulator 74 for receiving a power signal from the receiver 70 to energize the implantable cochlear stimulator circuits, including a processor 76. Data signals from the receiver 70 are also transmitted to the processor 76 where they are processed in order to generate stimulation signals that are applied to one or more of a plurality of capacitor coupled intracochlear electrodes 78.

In response to control or data signals from the wearable processor 46, the processor 76 selectively monitors voltages of the electrodes 78 and associated circuitry in the processor 76. For example, the processor 76 monitors the voltage applied to the regulator 74, current flowing through the electrodes 78, (from which an electrode impedance can be calculated) and other voltages within the processor 76, to generate the status-indicating signals which are sent to the telemetry transmitter 72 for transmission to the wearable system 40.

As is known in the art, the signals transmitted to the implantable cochlear stimulator 42 from the wearable system 40 include electrical power components. Such power components are processed within the receiver 70 through the series regulator 74 to generate a voltage signal which powers the implantable cochlear stimulator circuits, including the processor 76. The processor 76 selectively monitors the voltage applied to the series regulator 74 and generates a status indicating signal relative to such voltage, which is transmitted by the telemetry transmitter 72 and received by the telemetry receiver 66. As previously stated, such information is utilized in the microprocessor 60 and gate array 62 of the wearable processor 46 to control the power level of the transmissions from the data transmitter 64 to the implantable cochlear stimulator 42. The cochlear stimulator of FIG. 3 is described in more detail in the above-mentioned patent documents of Schulman, et al.

Figure 4:
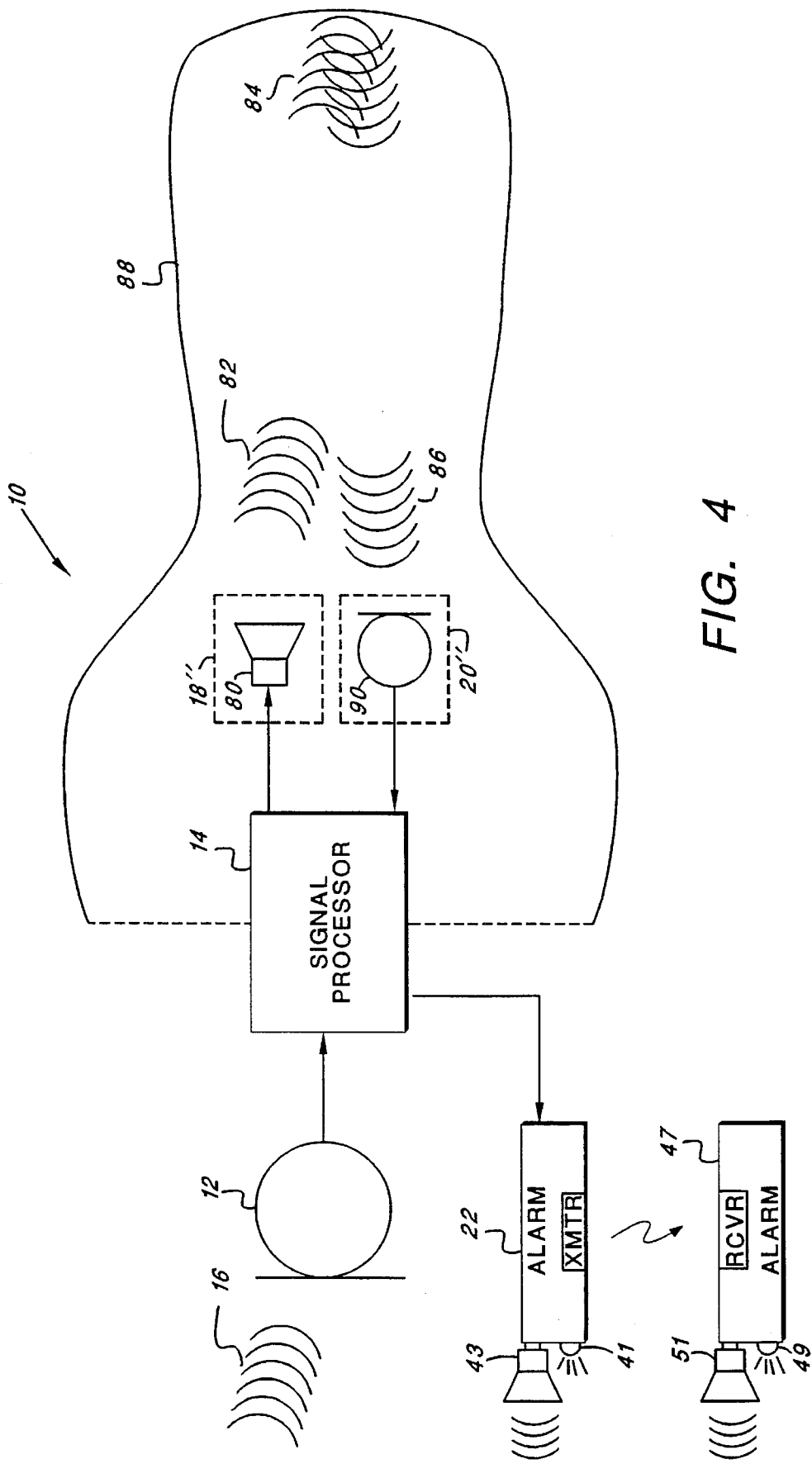
FIG. 4 is a block diagram of an amplifier-type hearing aid embodiment of the auditory response stimulator of FIG. 1.

Referring next to FIG. 4, a block diagram is shown of a hearing aid embodiment of the present invention. In the hearing aid embodiment, pressure waves 16 are received into the microphone 12 and the microphone signal is generated in response thereto. The microphone 12, being coupled to the signal processor 14, passes the microphone signal to the signal processor 14. The signal processor 14 may comprise an audio amplifier, which amplifies the microphone signal and generates the stimulation signal in response thereto. Such audio amplifiers are well known in the art.

The stimulation signal generated by the audio amplifier is used to energize the auditory response stimulator 18" which for the hearing aid embodiment, may be a speaker (ear phone) 80. In response to the stimulation signal, the speaker 80 generates stimulation waves 82, 84, 86 which are directed into an outer ear canal 88 of the patient, as is known in the art. The stimulation waves 82, 84, 86 are reflected by various surfaces within the outer ear canal 88 and are received back into the feedback device 20", which for the hearing aid embodiment may be an internal microphone 90. The internal microphone 90 then generates the feedback signal in response to the stimulation waves 82, 84, 86, and passes the feedback signal to the signal processor 14.

In the event the microphone 12 receives the pressure waves 16, but the speaker 80 does not generate the stimulation waves 82, 84, 86, or the internal microphone 90 does not receive the stimulation waves 82, 84, 86, the internal microphone 90 does not generate the feedback signal. As a result, the alarm signal will be generated, thereby signalling a fault in the auditory stimulation system 10, i.e., hearing aid. Note, however, that the alarm signal is not generated by the signal processor 14 in the event the microphone 12 does not receive the pressure waves 16, i.e., generation of the alarm signal is inhibited unless the pressure waves 16 are received by the microphone 12. This is because the speaker 80 does not, by design, generate the stimulation waves 82, 84, 86 unless the microphone 12 receives the pressure waves 16.

The hearing aid embodiment can also be used to detect and report distortions in the stimulation waves 82, 84, 86 by passing the information contained in the stimulation waves 82, 84, 86 back to the signal processor 14 in the feedback signal. Once the distorted information is back in the signal processor 14, its is compared with the undistorted information that was passed in the stimulation signal. By comparing the distorted information with the undistorted information, a determination can be made as to what level of distortion is being introduced by, e.g., the outer ear canal 88, and a signal-to-noise ratio (SNR) can be determined. When the SNR falls below a prescribed threshold, the alarm signal is generated by the signal processor 14 to indicate that, even though the stimulation signal is being received by the auditory response stimulator, it is so distorted that it is not reliable.

While the invention herein disclosed has been described by means of specific embodiments and applications thereof, numerous modifications and variations could be made thereto by those skilled in the art without departing from the scope of the invention set forth in the claims.

What is claimed is:

1. In a cochlear stimulator system comprising a wearable processor (wp) and an implantable cochlear stimulator (ICS), and wherein the WP includes a microphone for detecting audio signals, processing means for processing the detected audio signals, and first transceiver means for transmitting and receiving electrical signals to and from the ICS, and further wherein the ICS comprises second transceiver means for receiving and transmitting electrical signals from and to the WP, electrode means for making electrical contact with tissue to be stimulated, means for generating a stimulus signal in response to received electrical signals for application to the electrode means, and back telemetry means for generating telemetry signals for transmission back to the first transceiver means of the WP through the second transceiver means, a method for detecting failures comprising:

detecting an audio signal through the microphone;

generating a stimulation signal in response to the detected audio signal;

transmitting the stimulation signal to the second transceiver means of the ICS through the first transceiver means of the WP;

receiving the transmitted stimulation signal at the second transceiver means;

generating a feedback signal in the event the stimulation signal is received by the second transceiver means;

transmitting the feedback signal to the first transceiver means of the WP through the second transceiver means of the ICS;

generating an alarm signal to alert an operator in the event the feedback signal is not received by the second transceiver means.

2. The method of claim 1 further comprising:

coupling said stimulation signal through a skin surface of a patient; and coupling said feedback signal through the skin surface of the patient.

3. The method of claim 1 further comprising:

activating an alarm device in response to the generating of said alarm signal.

4. The method of claim 3 wherein said activating of said alarm device includes sounding an audible alarm.

5. The method of claim 4 wherein said activating of said alarm device further comprises: transmitting a radio frequency signal to a remote location;

receiving the radio frequency signal at the remote location; and sounding the audible alarm in response to receiving the radio frequency signal at the remote location.

6. The method of claim 3 wherein said activating of said alarm device comprises illuminating a light.

7. The method of claim 6 wherein said activating of said alarm device further comprises:

transmitting a radio frequency signal to a remote location;

receiving the radio frequency signal at the remote location; and illuminating the light in response to receiving of the radio frequency signal at the remote location.

8. Apparatus for detecting a failure in a cochlear stimulator comprising:

a microphone including means for sensing an audio signal;

a signal processor coupled to the microphone, the signal processor including means for generating a stimulation signal in response to the microphone sensing an audio signal;

a supercutaneous transmitter coupled to the signal processor, the supercutaneous transmitter including means for coupling the stimulation signal through a skin surface of a patient;

a subcutaneous receiver, including means for receiving the stimulation signal;

a subcutaneous transmitter coupled to the subcutaneous receiver, the subcutaneous transmitter including means for generating a feedback signal in response to receiving the stimulation signal by the subcutaneous receiver;

a supercutaneous receiver coupled to the signal processor, the supercutaneous receiver including means for receiving the feedback signal;

the signal processor including means for generating an alarm signal in the event the feedback signal is not received by the supercutaneous receiver.

9. The apparatus of claim 8 including:

an alarm device coupled to the supercutaneous receiver, the alarm device including means for indicating the presence of the alarm signal, whereby the alarm device is responsive to the alarm signal.

10. The apparatus of claim 11 wherein said alarm device includes means for sounding an audible alarm.

11. The apparatus of claim 12 wherein said alarm device further includes:

a radio frequency transmitter coupled to the supercutaneous receiver, the radio frequency transmitter including means for transmitting a radio frequency signal to a remote location in response to receipt of the alarm signal;

a remote radio frequency receiver including means for receiving the radio frequency signal at the remote location; and means coupled to the remote radio frequency receiver for sounding said audible alarm upon receipt of the radio frequency signal at the remote radio frequency receiver.

12. The apparatus of claim 9 wherein said alarm device includes a light and means for illuminating the light in response to receipt of the alarm signal.

13. The apparatus of claim 12 wherein said alarm device further includes:

a radio frequency transmitter coupled to the supercutaneous receiver, the radio frequency transmitter including means for transmitting a radio frequency signal to a remote location in response to receipt of the alarm signal;

a remote radio frequency receiver including means for receiving the radio frequency signal at the remote location; and means coupled to the remote radio frequency receiver for illuminating said light upon receipt of the radio frequency Signal at the remote radio frequency receiver.

14. Apparatus for detecting failures in a cochlear stimulator comprising:

microphone means for detecting an audio signal;

generating means for generating a stimulation signal in response to the microphone means detecting the audio signal, the generating means being coupled to the microphone means;

first transmitter means coupled to the generating means for telemetering the stimulation signal through a skin surface of a patient;

first receiver means for receiving the stimulation signal;

feedback means coupled to the first receiver means for generating a feedback signal in the event the stimulation signal is received by the first receiver means;

second transmitter means coupled to the feedback means for telemetering the feedback signal through the skin surface of the patient;

second receiver means coupled to the generating means for receiving the feedback signal; and alarm means coupled to the second receiver means for generating an alarm signal in the event the feedback signal is not received by the second receiver means, the alarm means including means for indicating the presence of the alarm signal.

15. The apparatus of claim 14 wherein said alarm means further includes:

transmitter means for transmitting a radio frequency signal to a remote location; and remote receiver means at the remote location for receiving the radio frequency signal; and means responsive to receipt of the radio frequency signal at the remote receiver means for generating the alarm signal and coupling the alarm signal to the alarm means.

\* \* \* \* \*